United States Patent
Pflug

(10) Patent No.: US 6,693,143 B2
(45) Date of Patent: Feb. 17, 2004

(54) DENTAL MATERIALS HAVING A NANOSCALE FILLER

(75) Inventor: Kai Pflug, Constance (DE)

(73) Assignee: Dentsply DeTrey GmbH (DE)

(*) Notice: Subject to any disclaimer, the term of this patent is extended or adjusted under 35 U.S.C. 154(b) by 183 days.

(21) Appl. No.: 10/015,214

(22) Filed: Nov. 19, 2001

(65) Prior Publication Data

US 2002/0065337 A1 May 30, 2002

Related U.S. Application Data

(62) Division of application No. 09/379,885, filed on Feb. 4, 1999, now Pat. No. 6,399,037, which is a continuation of application No. 09/156,164, filed on Sep. 17, 1998, now abandoned.

(60) Provisional application No. 60/060,910, filed on Oct. 3, 1997.

(51) Int. Cl.$^7$ ............................................. A61K 6/083
(52) U.S. Cl. ........................................ 523/116; 523/117
(58) Field of Search ................................. 523/116, 117

(56) References Cited

U.S. PATENT DOCUMENTS

| 4,297,266 A | 10/1981 | Ibsen et al. .................. 523/116 |
| 4,374,937 A | 2/1983 | Nemcek et al. .............. 523/116 |
| 4,389,497 A | 6/1983 | Schmitt et al. .............. 523/116 |
| 4,442,240 A | 4/1984 | Suh ............................. 523/116 |
| 4,512,743 A | 4/1985 | Santucci et al. ............. 433/217 |
| 4,544,359 A | 10/1985 | Waknine ..................... 523/115 |
| 4,552,906 A | 11/1985 | Podszun et al. ............. 523/115 |
| 4,617,327 A | 10/1986 | Podszun ..................... 523/116 |
| 4,629,746 A | 12/1986 | Michl et al. ................. 523/117 |
| 4,649,165 A | 3/1987 | Kuhlmann ................... 523/116 |
| 4,689,015 A | 8/1987 | Denyer et al. ............. 433/217.1 |
| 4,696,955 A | 9/1987 | Kuhlmann ................... 522/77 |
| 4,792,577 A | 12/1988 | Chen et al. ................. 523/118 |
| 4,839,401 A | 6/1989 | Waknine ..................... 522/14 |
| 5,228,907 A | 7/1993 | Eppinger et al. ............ 106/35 |
| 5,244,933 A | 9/1993 | Eidenbenz et al. ............ 522/3 |
| 5,334,625 A | 8/1994 | Ibsen et al. ................. 523/115 |
| 5,356,951 A | 10/1994 | Yearn et al. ................. 523/116 |
| 5,472,991 A | 12/1995 | Schmitt et al. ................ 522/4 |
| 5,859,716 A | 1/1999 | Ibsen et al. ................. 522/14 |
| 5,939,471 A | 8/1999 | Watanabe et al. ........... 523/334 |
| 5,990,195 A | 11/1999 | Arita .......................... 523/116 |
| 6,013,591 A | 1/2000 | Ying et al. ..................... 501/1 |
| 6,013,749 A | * 1/2000 | Baba et al. .................. 522/83 |

FOREIGN PATENT DOCUMENTS

| DE | 196 17 931 | 11/1997 |
| EP | 0 315 186 | 11/1988 |
| EP | 0 325 266 | 1/1989 |
| EP | 0 368 657 | 11/1989 |
| EP | 0 533 434 | 9/1992 |
| EP | 0 803 240 | 4/1997 |
| GB | 1 596 241 | 8/1981 |
| WO | 92/12698 | 8/1992 |

OTHER PUBLICATIONS

J. Osaka Univ., Dent. Sch.; vol. 35, 5~11, 1995; "Antibacterial Effect of Composite Incorporating Triclosan against *Streptococcus Mutans*".
B. Arkles, Chemtech 7, 766 (1977).
R. G. Craig, W. J. O'Brien, J.M. Powers, "Dental Materials, Properties and Manipulation" pp. 77–78, Mosby–Year Book, St. Louis (1992).

* cited by examiner

Primary Examiner—Peter Szekely
(74) Attorney, Agent, or Firm—Douglas J. Hura; James B. Bieber

(57) ABSTRACT

A low-viscosity dental material contains a non-settling nanoscale filler. Improvements of the mechanical properties of the dental materials, including the abrasive resistance and the compressive strength are provided. Furthermore, the dental materials have increased resistance to microleakage and have increased bond strengths. The filler forms a stable sol with low-viscosity dental materials and the filler may be prepared by surface treatment of fillers having a primary particle size of from about 1 to about 100 nanometers.

1 Claim, No Drawings

DENTAL MATERIALS HAVING A NANOSCALE FILLER

This is a divisional application of U.S. patent application Ser. No. 09/379,885 filed, Feb. 4, 1999, now U.S. Pat. No. 6,399,037, which is a Continuation of Ser. No. 09/156,164 filed Sep. 17, 1998, abandoned, which is filed from provisional application No. 60/060,910 filed Oct. 3, 1997.

TECHNICAL FIELD

The invention relates to low-viscosity dental materials containing a non-settling nanoscale filler. In particular, it relates to low-viscosity dental varnishes, dental sealants, and dental bonding agents containing a nanoscale filler and forming a stable sol with said filler. The filler improves the mechanical properties of the dental materials, e.g. the abrasion resistance and the compressive strength, and also improves their performance, e.g. it reduces microleakage and increases bond strengths.

A filler that forms stable sols with low-viscosity dental materials is prepared by surface treatment of very fine materials with suitable agents. Complete incorporation of the filler into the low-viscosity dental materials is achieved by employing high shear strengths such as with sonication.

BACKGROUND

Fillers of various sizes and types of materials are widely used in dental materials such as dental composites, compomers and cements. In these materials, fillers are employed to improve mechanical properties such as compressive strength, abrasion resistance, surface hardness and the like. Sometimes combinations of different particles sizes of fillers are used [e.g. U.S. Pat. No. 5,356,951]. Often the surface of the fillers has been chemically modified to become more compatible with the matrix [B. Arkles, Chemtech 7, 766 (1977)].

These materials typically have a high viscosity and a high filler content. Therefore settling of the filler in the uncured material is only a minor problem.

Other applications in dentistry demand dental materials that, as their characteristic property, display a low viscosity. Typical examples for materials of this type are dental bonding agents [R. G. Craig, W. J. O'Brien, J. M. Powers, "Dental Materials, Properties and Manipulation", p. 77–78, Mosby-Year Book, St. Louis 1992] and dental varnishes. For optimum performance, these materials have to deeply penetrate the dentin. This is something that can only usually be achieved by materials with a low viscosity and good wetting properties. However, even with these materials, the clinical performance can be improved by increasing the hardness and mechanical strength of the cured material. Potentially, incorporation of filler into these low-viscosity dental bonding agents, dental varnishes and other dental materials can increase their mechanical strength. Nevertheless, these low-viscosity dental materials rarely contain filler.

The density of filler and the matrix material differs considerably. While most known fillers have a density of >2 g/ml (gram/milliliter), most matrix materials, e.g. solvents or resins, have densities of about 1 g/ml or below. Therefore, even if the polarity of the filler surface and of the matrix are compatible, some settling of filler occurs due to the difference in densities.

Raising the filler content up to a level where settling is impossible also leads to a drastic increase in viscosity which for the type of materials that have to penetrate the dentin to work properly, is not acceptable.

Therefore, there is a need for a filler that can be evenly distributed in a low-viscosity dental material to form a stable sol without drastically increasing the viscosity of the dental material.

This filler, if properly selected, will improve the physical properties of the low-viscosity dental materials with which it is employed.

SUMMARY OF THE INVENTION

It is an object of the invention to provide low-viscosity dental materials comprising a nanoscale filler. The nanofiller content in the low-viscosity dental materials improves properties that are clinically relevant for said materials. For example, for a protective dental varnish, the nanofiller content increases abrasion resistance and surface hardness. For a dental bonding agent, the nanofiller content increases adhesion to both enamel and dentin and improves marginal integrity.

The nanofiller provided by this invention has a mean primary particle size of about 1 nm to about 100 nanometers (nm). It is prepared from fine fillers such as glass, alumina, silica and the like by chemically modifying the surface in a non-aqueous solvent followed by drying. The filler is then incorporated into the low-viscosity dental material by applying high shear forces, e.g. by sonication. This incorporation leads to the nanofiller forming a stable, non-settling sol with the low-viscosity dental material.

These and other objects of the invention which shall be apparent from the specification to follow, are accomplished by the invention as hereinafter described and claimed.

In general, a dental material comprises a nanoscale filler having a primary particle size of from about 1 nm to about 100 nm. The filler may be selected from the group selected of ground glass, ground quartz, highly dispersed silica, zeolite, laponite, kaolinite, vermiculite, mica, ceramic metal oxides, alumina, pyrogenic silica, sparingly volatile oxides of titanium, zirconium, germanium, tin, zinc, iron, chromium, vanadium, tantalum, niobium, and mixtures thereof.

DETAILED DESCRIPTION OF THE INVENTION

The present invention provides low-viscosity dental materials comprising a nanoscale filler. The nanofiller content in the low-viscosity dental materials improves properties that are clincially relevant for said materials.

A preferred range of nanofiller is from about 0.01 to about 20 percent by weight based upon 100 percent by weight of the dental material.

From about 10 to about 90 percent by weight of polymerizable materials are provided to form the polymeric network. Useful polymerizable materials include methacrylate and acrylate monomers having at least one saturated double bond, and mixtures thereof. Preferred polymerizable monomers are those that are curable, more preferably, light-curable.

The dental materials described in this invention may comprise solvents. Useful solvents include water, acetone, ethanol, ethyl acetate and other organic solvents with boiling points below that of water. A useful amount of solvent would be from about 10 to about 90 percent of weight of the dental material.

The dental materials may include resins, fillers other than nanoscale fillers, stabilizers, initiators, fluorides, solvents and other substances commonly used in dental materials.

The dental materials described in the present invention comprise polymerizable monomers and nanoscale fillers in a stable sol of low viscosity. The low viscosity allows deep penetration of the dentin, resulting in good adhesion to the dentin and mechanical strengthening of the dentin. The nanofiller particles incorporated into the dental materials enforces these properties. By "low-viscosity" as used herein, it is meant from about 0.0001 to about 1 Pas.

By "nanoscale filler" or "nanofiller" it is meant materials having a primary particle size of from about 1 nm to about 100 nm. By "primary particle size" is meant that with powders, the primary particles are the smallest homogeneous particles. The term is used to determine primary from secondary particles that may form by agglomeration or aggregation of primary particles and are therefore necessarily larger than the primary particles. For example, with Aerosil 380 as discussed below, the primary particle size is approximately 7 nm but there may be agglomerates or aggregates of these primary particles having a larger size. Of course, these larger secondary particles are still within the scope of the invention. However, by "primary particles" is meant those that would remain after destruction of agglomerates and aggregates.

Examples of useful starting materials for the nanofillers described in the present invention include ground glass or quartz, highly dispersed silica, zeolite, laponite, kaolinite, vermiculite, mica, ceramic metal oxides, alumina, pyrogenic silica, sparingly volatile oxides of titanium, zirconium, germanium, tin, zinc, iron, chromium, vanadium, tantalum, niobium, and mixtures thereof. Preferred useful starting materials have to have a primary particle size of about 1 nm to about 100 nm.

For synthesis of the nanofiller described in the present invention, these materials are treated with an agent enabling the filler to form a stable sol in an organic solution with a viscosity of about 1 Pas. It is preferred to carry out this treatment in a non-aqueous solvent to prevent agglomeration of the filler particles.

Silanating agents are preferred, and it is further preferred to treat the filler before formation of the sol. Sol formation will be more fully described below.

Preferred silanating agents include those having at least one polymerizable double bond and at least one group that easily hydrolyses with water. Examples of such agents include 3-methacryloxypropyltrimethoxysilane, 3-methacryloxypropyldimethoxy-monochlorosilane, 3-methacryloxypropyldichloromonomethoxysilane, methacryloxypropyltri-chlorosilane, 3-methacryloxypropyldichloromonomethyl-silane, 3-methacryloxypropylmonochlorodimethylsilane, and mixtures thereof. These agents are preferably employed in a non-aqueous solution.

After drying of the filler materials treated with these agents, incorporation of the nanofiller is preferably done by mixing the nanofiller with the low-viscosity dental material and employing high shear strengths, e.g. with an Ultraturrax mixer or by sonication. As will be shown in the following examples, the nanofiller forms stable sols of low viscosity and improves relevant mechanical properties of dental materials. If used in a dental varnish, the nanofiller increases the abrasion resistance and the surface hardness. As a component of a dental bonding agent, the nanofiller improves bond strengths and marginal integrity of the bonding agent.

For some applications, thin films are necessary. For example, a cervical dental varnish should not be visible and therefore has to be thin. A colourless adhesive agent used to fix an inlay to tooth structure should be thin as no gap between the inlay and the tooth should be seen.

The lowest film thickness achievable with a given material depends on the viscosity of the material. Therefore low-viscosity film formers are preferable to achieve thin films. To get thin, hard films therefore fillers can only be employed if they do not significantly increase the viscosity of the film former and if their particle size is significantly lower than that of the film to be obtained. Nanofillers as described in Example 1 below meet these requirements and may therefore be employed to obtain thin, hard films. Thin films according to the invention have a film thickness of from about 1 to about 50 nm.

EXAMPLES

Example 1

Synthesis of Nanofiller

Incorporation of fillers into dental materials of low viscosity requires the synthesis of special material. The filler has to be capable of forming a stable sol with the low viscosity materials to avoid settling of the filler.

According to the present invention, Aerosil 380 silanated in an organic solvent is one preferred nanofiller. It is shown to form stable sols with low-viscosity dental materials after ultrasonic treatment.

Aerosil 380, available from Degussa is a silica with a BET surface area (as discussed in DIN 53 200) of 380 $m^2/g$, a primary particle size of 7 nm and 2–3.3 OH groups/$nm^2$, at 2.7 OH groups/$nm^2$ this corresponds to 1.7 mmol (millimols) OH/g Aerosil 380. The letter "m" stands for meters.

A large number of silanated Aerosil 380 fillers were synthesized. The synthesis of a number of fillers is described below.

KP2-121-1:
Eight g Aerosil 380 (undried) and 1.19 g 3-methacryloxypropyl-trichlorosilane were refluxed in 135 g toluene (dried over molecular sieve) for 15 hours (h). The reaction product was dried.

The amount of silane employed corresponds to a silylation of approximately 100% of surface OH groups.

KP2-121-2:
Eight g Aerosil 380 (undried) and 3.56 g 3-methacryloxypropyl-trichlorosilane were refluxed in 135 g toluene (dried over molecular sieve) for 15 h. The reaction product was dried. The amount of silane employed corresponds to a silylation of approximately 300% of surface OH groups.

KP2-123-1:
Eight g Aerosil 380 (undried) and 1.64 g 3-methacryloxypropylmethyl-dichlorosilane were refluxed in 135 g toluene (dried over molecular sieve) for 15 h. The reaction product was dried.

KP2-123-2:
Eight g Aerosil 380 (undried) and 3.28 g 3-methacryloxypropylmethyl-dichlorosilane were refluxed in 135 g toluene (dried over molecular sieve) for 15 h. The reaction product was dried.

KP2-126-1:
Eight g Aerosil 380 (dried for 4 d at 120° C.) and 1.19 g 3-methacryloxypropyl-trichlorosilane were refluxed in 135 g toluene (dried over molecular sieve) for 15 h. The reaction product was dried.

KP2-126-2:

Eight g Aerosil 380 (dried for 4 d at 120° C.) and 3.56 g 3-methacryloxypropyl-trichlorosilane were refluxed in 135 g toluene (dried over molecular sieve) for 15 h. The reaction product was dried.

KP2-128-1:

Eight g Aerosil 380 (undried) and 1.64 g 3-methacryloxypropylmethyl-dichlorosilane were refluxed in 135 g toluene (dried over molecular sieve) for 15 h. The reaction product was dried.

KP2-128-2, KP2-131-1 and KP2-131-2 were synthesized accordingly. The silanes employed are listed in the table below.

To control the silantation of the Aerosil 380, a simple hydrophobicity test was carried out. The silanated Aerosil was powdered, and a smooth surface was created by applying pressure to the material with a glass plate. A drop of water was placed on top of the smooth surface, and the time until vanishing of the drop of water was measured. This method allows a rough comparison of hydrophobicity as with more hydrophilic materials, the water penetrates them more rapidly.

Table I: hydrophobic behavior of Aerosil 380 silanated with different agents and ratios (M:3-methacryloxypropyl): the time a drop of water needed to penetrate into the material was measured (long penetration time=hydrophobic material).

| CODE | SILANE | RATIO Cl/OH | PRE-TREATMENT OF AEROSIL | PENE-TRATION TIME (H) |
|---|---|---|---|---|
| KP2-121-1 | MSiCl$_3$ | 1:1 | undried | 0 |
| KP2-121-2 | MSiCl$_3$ | 3:1 | undried | 5 |
| KP2-123-1 | MSiMeCl$_2$ | 1:1 | undried | 1 |
| KP2-123-2 | MSiMeCl$_2$ | 2:1 | undried | >5 |
| KP2-126-1 | MSiCl$_3$ | 1:1 | dried | 0 |
| KP2-126-2 | MSiCl$_3$ | 3:1 | dried | 1 |
| KP2-128-1 | MSiMeCl$_2$ | 1:1 | dried | 1.5 |
| KP2-128-2 | MSiMeCl$_2$ | 2:1 | dried | 3 |
| KP2-131-1 | MSiMe$_2$Cl | 1.3:1 | dried | 4 |
| KP2-131-2 | MSi(OMe)$_3$ | 4.5:1* | dried | 0 |

*(OMe/OH)

One percent of these silanated glass fillers were suspended in a mixture of 81 weight percent (wt %) acetone, 13 wt % UDMA (urethane dimethacrylate) and 6 wt % PENTA (dipentaerythritol pentaacrylate monophosphate). The mixtures were put into an ultrasonic bath for 3 hours. The mixtures were then left undisturbed. After 3 hours, the suspensions were checked for settling of material.

No settling of filler was observed using the fillers KP2-121-1, KP2-123-1, KP2-123-2, KP2-128-1 and KP2-131-1.

Very little settling of filler was observed with fillers KP2-126-1 and KP2-128-2.

Little settling was observed with fillers KP2-121-2 and KP2-126-2.

Some settling was observed with filler KP2-131-2.

The mixture with KP2-131-1 was left undisturbed for 5 months. Only a very small initial settling of filler could be observed. This small amount of filler could easily be resuspended by shaking the mixture, or filtered off. The remaining material then stayed clear without settling of nanofiller.

The results show that by silanation of Aerosil 380 in toluene, it is possible to obtain a hydrophobic filler if an excess of silane is used.

Silanation can also be proven by IR spectroscopy as the methacrylate group of the silane displays a strong carbonyl peak.

Example 2

Protective Varnish Containing Nanofiller

This example demonstrates the efficacy of the nanoscale filler to increase surface hardness and abrasion resistance of a low-viscosity dental varnish formulation.

A protective varnish for exposed dentin was prepared containing the components listed below:

| Composition 1: | |
|---|---|
| ~80 wt % | acetone |
| ~10.5 wt % | UDMA-resin (2,7,7,9,15-pentamethyl-4,13-dioxo-3,14-dioxa-5,12-diaza-hexadecan-1,16-diyldimethacrylate) |
| ~4.8 wt % | PENTA (dipentaerythritol pentaacrylate monophosphate) |
| ~3.0 wt % | urethane resin R5-62-1 (7,7,9,63,63,65-Hexamethyl-4,13,60,69-tetraoxo-3,14,19,24,2934,39,44,49,54,59,70-dodecanoxa-5,12,61,68-tetraaza-doheptaconta-1,72-diyldimethacrylate) |
| ~0.6 wt % | ethyl 4-dimethylaminobenzoate |
| ~0.1 wt % | 2,6-di-tert-butyl-p-cresol |
| ~0.2 wt % | cetylamine hydrofluoride |
| ~0.6 wt % | trimethylolpropane trimethacrylate |
| ~0.2 wt % | camphorquinone |

To this mixture (100% wt), nanofiller was added (for synthesis see Example 1). Formation of a homogenous sol occurred after sonication for 30 min.

This varnish had a low viscosity and deeply penetrated dentin. After application, the acetone solvent was removed by air-drying. Curing was done with a dental curing lamp with visible light for 20 seconds. A thin, strong polymeric film (thickness approximately 2–6 µm) remained.

To demonstrate the effect of nanofiller on the hardness of the varnish, plaques of approximately 1.2 g (width 2 mm, diameter 25 mm) with varying nanofiller contents were made from a mixture of the varnish components except for the solvent. The plaques were light-cured, and Barcol hardness was measured.

The hardness of the varnish containing nanofiller was found to be higher as the hardness of the varnish not containing nanofiller.

TABLE II

Barcol harness of resin mixtures containing nanofiller glass

| CODE MIXTURE | CODE RESIN | CODE GLASS | GLASS (wt %)* | BARCOL HARDNESS |
|---|---|---|---|---|
| | KP2-55 | — | — | 40.7 ± 0.7 |
| | BEH1-4-1 | — | — | 41.0 ± 2.2 |
| | BEH1-4-1 | — | — | 42.4 ± 1.8 |
| KP2-121-1 | KP2-55 | KP2-121-1 | 5 | 46.5 ± 1.2 |
| KP2-121-2 | KP2-55 | KP2-121-2 | 5 | 43.6 ± 1.6 |
| KP2-123-1 | KP2-55 | KP2-123-1 | 5 | 45.6 ± 1.7 |
| KP2-123-2 | KP2-55 | KP2-123-2 | 5 | 46.9 ± 3.3 |
| KP2-126-1 | KP2-55 | KP2-126-1 | 5 | 46.4 ± 0.8 |
| KP2-126-2 | KP2-55 | KP2-126-2 | 5 | 44.8 ± 1.6 |
| KP2-128-1 | KP2-55 | KP2-128-1 | 5 | 44.8 ± 1.5 |
| KP2-128-2 | KP2-55 | KP2-128-2 | 5 | 45.4 ± 1.7 |
| BEH1-14-1 | BEH1-4-1 | KP2-131-1 | 5 | 44.5 ± 1.6 |
| BEH1-14-2 | BEH1-4-1 | KP2-131-2 | 5 | 45.6 ± 2.4 |
| BEH1-31-3 | BEH1-4-1 | KP2-131-1 | 7 | 46.3 ± 1.6 |
| BEH1-31-4 | BEH1-4-1 | KP2-131-1 | 8 | 45.9 ± 1.1 |
| BEH1-31-5 | BEH1-4-1 | KP2-131-1 | 9 | 46.7 ± 1.4 |

*based on resin

The incorporation of nanofiller glass into the varnish formulation clearly increases the hardness of the cured polymer.

To demonstrate the effect of the nanofiller on the abrasion resistance of the varnish, plates were covered with the resin base of experimental varnish formulations (containing all components except for the solvent). The varnish coat was then light-cured and subjected to an abrasion-resistance test using a Taber Abraser 5130. In this test, weight losses of varnish coats applied to steel plates were measured after 400 cycles using rubber rolls CS-O in combination with abrasive paper S-33 and a weight of 1 kg on the rolls.

For a varnish coat of composition 2 (no nanofiller), a weight loss of 1.13 g after 400 cycles was found. For composition 3 (composition 1+9% nanofiller BEH1-76-1, which was synthesized as described for KP2-131-1), a weight loss of only 0.79 g was found after 400 cycles. Incorporation of 9% nanofiller therefore leads to a reduction in abrasion of 30%. For similar formulations, a reduction in abrasion of between 30% and 39% was found by incorporation of 9% nanofiller.

| Composition 2: | |
|---|---|
| –52.5 wt % | UDMA-resin (2,7,7,9,15-pentamethyl-4,13-dioxo-3,14-dioxa-5,12-diaza hexadecan-1,16-diyldimethacrylate) |
| –24 wt % | PENTA (dipentaerythritol pentaacrylate monophopsphate) |
| –15 wt % | urethane resin R-5-62-1 (7,7,9,63,63,65-Hexamethyl-4,13,60,69-tetraoxo-3,14,19,24,29,34,39,44,49,54,59,70-dodecanoxa-5,12,61,68-tetraaza-doheptaconta-1,72-diyldimethacrylate) |
| –3 wt % | ethyl 4-dimethylaminobenzoate |
| –0.5 wt % | 2,6,di-tert-butyl-p-cresol |
| –1.0 wt % | cetylamine hydrofluoride |
| –3.0 wt % | trimethylolpropane trimethacrylate |
| –1.0 wt % | camphorquinone |

Composition 3:
Composition 2 (100 wt %) plus nanofiller BEH1-76-1 (9 wt %)

A useable varnish formulation has to have a low viscosity to be capable of sufficiently penetrating the dentin. Any filler incorporated into the varnish formulation therefore should form a stable sol in the low-viscosity varnish.

For sol formulation, a useful method is to mix filler and varnish solution and to put the mixture in an ultrasonic bath for 30 min. For a varnish formulation prepared this way from filler KP2-131-1 and a varnish solution, a stability of greater than 3 months has been proven (filler concentration was 1 wt %, composition as described above).

Example 3

Dental Bonding Agent Containing Nanofiller

This example demonstrates the efficacy of the nanoscale filler to improve marginal quality and increase bond strengths of a low-viscosity dental bonding agent formulation.

A dental bonding agent was prepared containing the following components:

| Composition 4: | |
|---|---|
| –80 wt % | acetone |
| –10.5 wt % | UDMA-resin (2,7,7,9,15-pentamethyl-4,13-dioxo-3,14-dioxa-5,12-diaza hexadecan-1,16-diyldimethacrylate) |
| –4.8 wt % | PENTA (dipentaerythritol pentaacrylate monophopsphate) |
| –0.6 | ethyl 4-dimethylaminobenzoate |
| –0.1 wt % | 2,6,di-tert-butyl-p-cresol |

| -continued | |
|---|---|
| Composition 4: | |
| –0.2 wt % | cetylamine hydrofluoride |
| –3.6 wt % | trimethylolpropane trimethacrylate |
| –0.2 wt % | camphorquinone |

To this composition (100 wt %), various amounts of filler KP2-131-1 were added. A stable sol was formed by sonication for 30 minutes (min). The resulting formulations were then tested for shear bond strengths to both dentin and enamel.

For purposes of enamel bond tests, the enamel surface of 6 human molars was polished with carborund (SiC). This fresh, dry enamel surface was treated with a 5% maleic acid/5% itaconic acid solution for 20 seconds, followed by compressed air drying. Thereafter, the experimental dental bonding agent was applied and, 20 seconds later, compressed air drying was effected. This coat was light-cured for 20 seconds, using a Spectrum curing light (available from DENTSPLY International Inc.). Subsequently, a plastic mold with an inner diameter of 5 mm and a height of 2 mm was fixed to the surface and TPH Spectrum was filled into the interior of the mold. The surface was subjected to visible light irradiation by the Spectrum curing light via the mold for 40 seconds. After light-curing, the teeth were stored at 37° C. for 24 hours, then thermocycled 500 times (20 seconds at 5° C., 20 seconds at 55° C.), embedded in gypsum and tested with a Zwick Z010/TN2A tabletop universal testing machine at a speed of 1 mm/min.

For purposes of dentin bond tests, the dentin surface of 6 human molars was exposed with a diamond saw and ground with No. 500 sandpaper. This fresh dentin surface was treated with a 5% maleic acid/5% itaconic acid solution for 20 seconds followed by careful drying with a paper towel. This drying should leave a dry-looking surface but should not be too harsh. Thereafter, the experimental bonding agent was applied and, 20 seconds later, compressed air drying was applied. This coat was light-cured for 20 seconds, using a Spectrum curing light (Dentsply). Subsequently, a plastic mold with an inner diameter of 5 mm and a height of 2 mm was fixed to the surface and TPH Spectrum (DENTSPLY) was filled into the interior of the mold. The surface was subjected to visible light irradiation by the Spectrum curing light via the mold for 40 seconds. After light-curing, the teeth were stored at 37° C. for 24 hours, then thermocycled 500 times (20 seconds at 5° C., 20 seconds at 55° C.), embedded in gypsum and tested with a Zwick Z010/TN2A tabletop universal testing machine at a speed of 1 mm/min.

The results of these tests are listed in Table III below.

TABLE III

Adhesion of experimental dental bonding agents containing nanofiller

| CODE | WT % FILLER | ADHESION TO ENAMEL (MPa) | ADHESION TO DENTIN (MPa) | % COHESIVE FAILURE DENTIN |
|---|---|---|---|---|
| BEH1-47-1 | — | 13.4(35) | 15.4(14) | 30 |
| BEH1-47-2 | 1 | 13.4(14) | 23.6(21) | 50 |
| BEH1-48-2 | 1.8 | 17.5(30) | 21.2(24) | 100 |

The table shows that the nanofiller content does increase shear bond strength to both enamel and dentin. It also leads to an increase in cohesive failures in dentin, another indicator of an increase in shear bond strengths.

Marginal integrity of dental bonding agents containing nanofiller in class II cavities was investigated. Marginal integrity was investigated before and after applying an intermitting load of 10–125 N (Newtons) at 52 cycles/min (4000 x where "x" is "times") by examining the penetration of an aqueous methylene blue solution into the interface between tooth and restorative material. The penetration (marginal leakage) was classified into various groups depending on the depth of penetration. Both penetration on the cervical and on the occlusal margin were determined. Pretreatment was with a 5% maleic acid/5% itaconic acid solution without rinsing followed by 1 coat of bonding agent with curing. In all cases, cavities with butt joint enamel margins were restored with Dyract (DENTSPLY) as restorative material.

Two different composition of bonding agents were used:

| | Composition 5: |
|---|---|
| –50 wt % | acetone |
| –26.25 wt % | UDMA-resin (2,7,7,9,15-pentamethyl-4,13-dioxo-3,14-dioxa-5,12-diaza hexadecan-1,16-diyldimethacrylate) |
| –12.0 wt % | PENTA (dipentaerythritol pentaacrylate monophopsphate) |
| –7.5 wt % | urethane resin R5-62-1 (7,7,9,63,63,65-Hexamethyl-4,13,60,69-tetraoxo-3,14,19,24,29,34,39,44,49,54,59,70-dodecanoxa-5,12,61,68-tetraaza-doheptaconta-1,72-diyldimethacrylate) |
| –1.5 wt % | ethyl 4-dimethylaminobenzoate |
| –0.25 wt % | 2,6,di-tert-butyl-p-cresol |
| –0.5 wt % | cetylamine hydrofluoride |
| –1.5 wt % | trimethylolpropane trimethacrylate |
| –0.5 wt % | camphorquinone |

Composition 6:

Composition 4 (100 wt %) plus 4.5 wt % nanofiller BEH1-76-1 (synthesized as KP2-131-1)

On the cervical margin, the following criteria were used:

| 0 | no penetration |
|---|---|
| 1 | penetration along ⅓ of the gingival wall |
| 2 | penetration along ⅔ of the gingival wall |
| 3 | penetration along the entire gingival wall |
| 4 | penetration along the whole length of the gingival wall and up to the axial wall. |

On the occlusal margin, the following criteria were used:

| o | no penetration |
|---|---|
| a | penetration along the enamel wall |
| b | penetration along the entire enamel/dentin wall |
| c | penetration beyond the wall/bottom corner along the bottom of the step |

Results—Cervical Margin

For the control group (Composition 5, no nanofiller), dye penetration at the cervical margin before load was

| 90% category 0 |
|---|
| 10% category 1 |

After load, dye penetration was

| 30% category 0 |
|---|
| 40% category 1 |
| 10% category 2 |
| 20% category 3 |

For the experimental group (Composition 6, contains nanofiller), dye penetration at the cervical margin before load was

| 100% category 0 |
|---|
| 0% category 1 |

After load, dye penetration was

| 70% category 0 |
|---|
| 30% category 1 |

The results of the bonding agent containing nanofiller are considerably better than those of the control group.

Results—Occlusal Margin

For the control group (Composition 5, no nanofiller), dye penetration at the occlusal margin before load was

| 90% category o |
|---|
| 10% category a |

After load, dye penetration was

| 30% category o |
|---|
| 40% category a |
| 30% category b |

For the experimental group (Composition 6, contains nanofiller), dye penetration at the occlusal margin before load was

| 100% category o |
|---|
| 0% category a |

After load, dye penetration was

| 80% category o |
|---|
| 20% category a |

The results of the bonding agent containing nanofiller are considerably better than those of the control group.

Example 4

Dental Sealant Containing Nanofiller

Dental sealants should have a low viscosity to deeply penetrate fissures while also having a sufficient hardness and abrasion resistance. Nanofillers as described in Example 1

(e.g. in a composition similar to composition 3) will raise the hardness and abrasion resistance of the cured material while not significantly increasing the viscosity of the sealant, thus making complete fissure penetration more likely.

The materials according to the present invention may also be used as desensitizing agents under for example, cemented crowns. Examples of such crowns are those cemented with glass ionomer and zinc phosphate cement. Although the invention has been exemplified above for use with materials such as Dyract and Prisma TPH for DENTSPLY International Inc., it is understood that the invention can be used with other materials such as Enforce, also available from DENTSPLY International Inc.

The foregoing examples and description of preferred embodiments of the present invention are provided for the purposes of illustration and description. The examples and preferred embodiments, however, are not intended to be exhaustive or limit the invention to the precise forms disclosed. Modifications and variations will be apparent to those skilled in the art. The embodiments provided explain the principals of the invention and its practical application, thereby enabling others skilled in the art to understand the invention for various embodiments and with various modifications as are suited to the particular use contemplated. It is intended that the scope of the invention be defined by the following claims and their equivalents.

What is claimed is:

1. A dental material comprising a polymerizable material and filler;

said polymerizable material being selected from the group consisting of methacrylate and acrylate monomers having at least one polymerizable double bond, and mixtures thereof;

said filler comprising a nanoscale material with a particle size of about 1 nm to about 100 nm, wherein said nanoscale material is prepared by chemical surface treatment, said surface treatment enabling the nanoscale material to form a stable sol with dental materials of a viscosity of below about 1 Pas, wherein said surface treatment includes silanating said nanoscale material in a non-aqueous solvent; wherein the silanating agent has at least one polymerizable double bond and at least one group that hydrolyses with water; wherein the silanating agent is selected from the group consisting of
   3-methacryloxypropyldimethoxy-monochlorosilane,
   3-methacryloxypropyldichloromonomethoxysilane,
     methacryloxypropyltrichlorosilane,
   3-methacryloxypropyldichloromonomethyl-silane,
   3-methacryloxypropylmonochlorodimethylsilane, and mixtures thereof; and wherein said material is selected from the group consisting of ground glass, ground quartz, highly dispersed silica, zeolite, laponite, kaolinite, vermiculite, mica, ceramic metal oxides, alumina, pyrogenic silica, sparingly volatile oxides of titanium, zirconium, germanium, tin, zinc, iron, chromium, vanadium, tantalum, niobium, and mixtures thereof;

wherein the dental material has a viscosity of from about 0.0001 Pas to about 1 Pas.

* * * * *